United States Patent [19]

Berger

[11] Patent Number: 5,735,823
[45] Date of Patent: Apr. 7, 1998

[54] SAFETY SYRINGE WITH I.V. PORT ACCESS

[75] Inventor: Howard S. Berger, Hackensack, N.J.

[73] Assignee: Becton, Dickinson and Company, Franklin Lakes, N.J.

[21] Appl. No.: 335,214

[22] Filed: Nov. 7, 1994

Related U.S. Application Data

[63] Continuation of Ser. No. 910,196, Jul. 8, 1992, abandoned.
[51] Int. Cl.6 .................................................... A61M 5/32
[52] U.S. Cl. .......................... 604/192; 604/198; 604/284; 604/905
[58] Field of Search .................................. 604/192, 187, 604/198, 263, 83–87, 283, 284, 905

[56] References Cited

U.S. PATENT DOCUMENTS

| Re. 33,617 | 6/1991 | Ogle, II . | |
|---|---|---|---|
| 4,232,669 | 11/1980 | Nitshke . | |
| 4,631,057 | 12/1986 | Mitchell . | |
| 4,759,756 | 7/1988 | Forman et al. . | |
| 4,834,716 | 5/1989 | Ogle, II . | |
| 4,840,619 | 6/1989 | Hughes . | |
| 4,946,445 | 8/1990 | Lynn | 604/192 |
| 4,998,921 | 3/1991 | Vickroy et al. . | |
| 4,998,924 | 3/1991 | Ranford . | |
| 5,088,985 | 2/1992 | Deras | 604/192 |
| 5,151,090 | 9/1992 | Best et al. | 604/86 X |
| 5,195,993 | 3/1993 | Gianakos | 604/198 X |

FOREIGN PATENT DOCUMENTS

| 909008 | 11/1990 | South Africa . |
|---|---|---|
| 678600A5 | 10/1991 | Switzerland . |
| 8910770 | 11/1989 | WIPO . |

*Primary Examiner*—John D. Yasko
*Attorney, Agent, or Firm*—Arthur D. Dawson

[57] ABSTRACT

A safety needle device which can be used substantially as a regular syringe or with a "y" connector. The device includes an elongate barrel with a longitudinal axis and an inside surface defining a chamber which has an open proximal end and a distal end with a needle cannula. The needle cannula projects distally outwardly, and has a distal tip and a lumen in fluid communication with the barrel chamber. The device has a needle guard with a proximal first end and a distal second end. The guard is mounted for movement relative to the barrel from a retracted position in which the guard does not materially obstruct access to the distal tip of the needle cannula and an extended position where the guard substantially prevents inadvertent access to the distal tip of the needle cannula.

The needle guard is releasably retained in the retracted position and locks in the extended position. The guard has at least one open slot which extends proximally from the second end. The slot is sized to accept the sidearm of a "y" connector when the needle penetrates the septum of the "y" connector and the bore of the connector is in fluid communication with the chamber of the barrel.

5 Claims, 5 Drawing Sheets

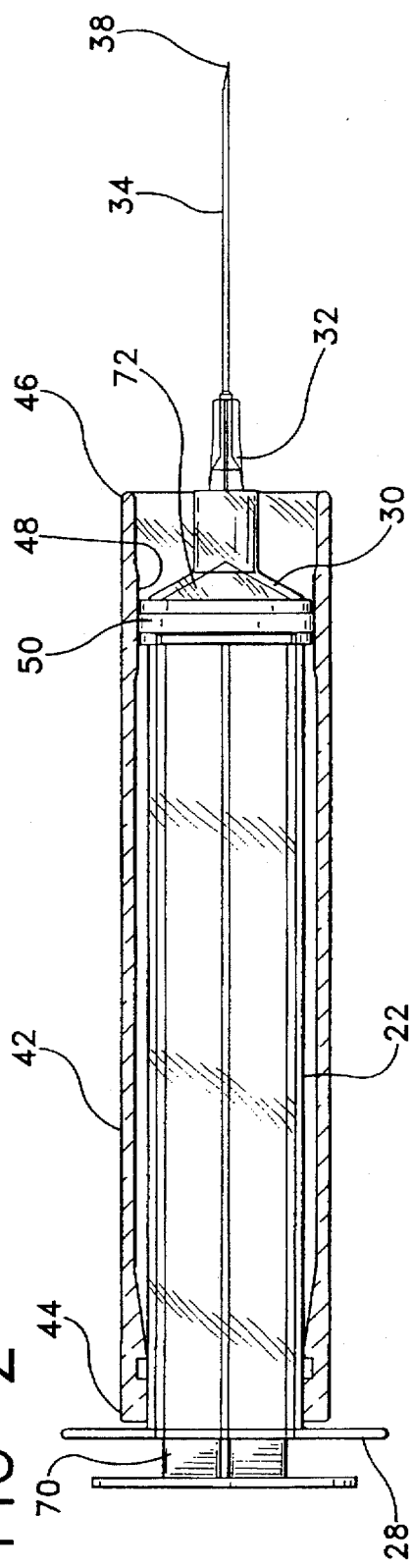
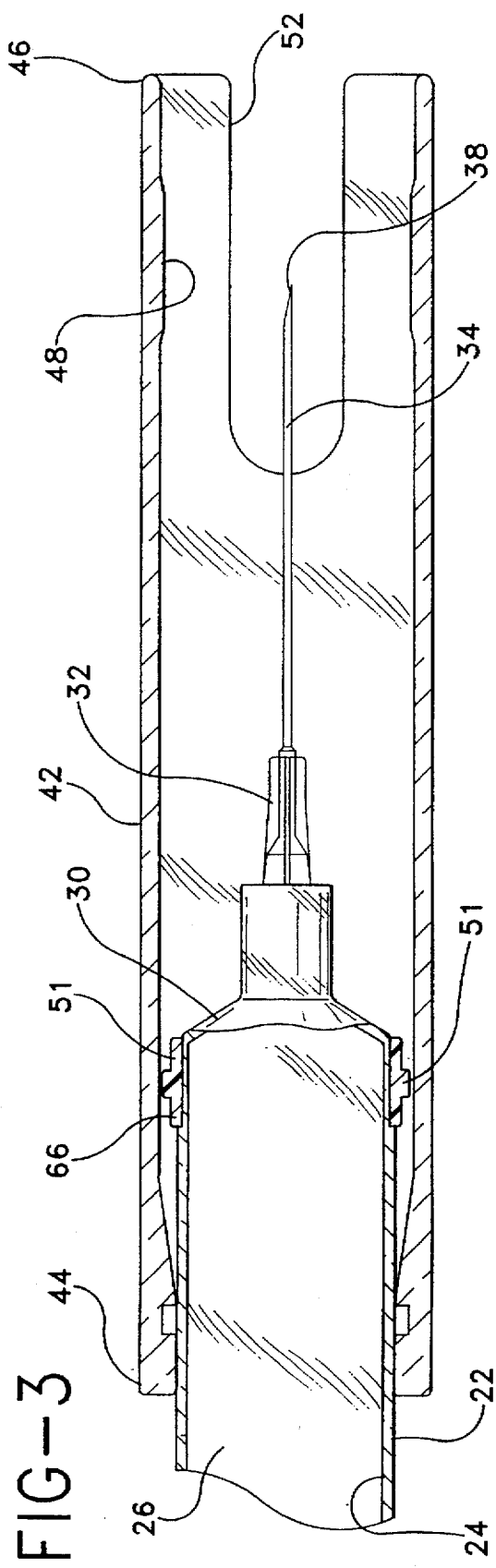

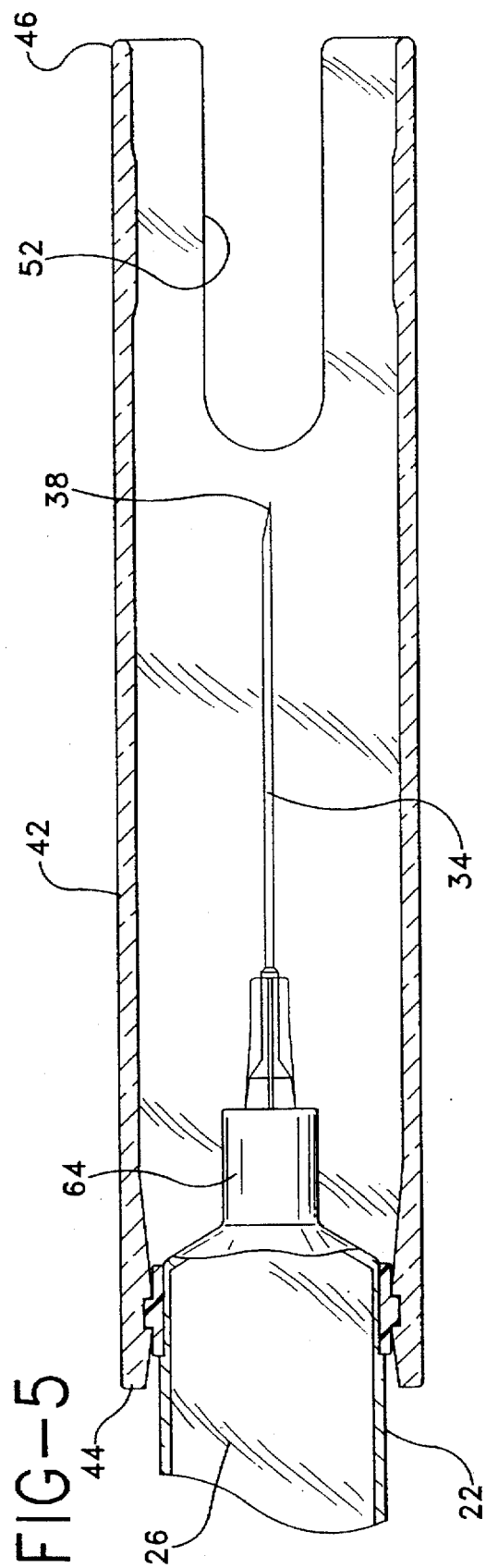
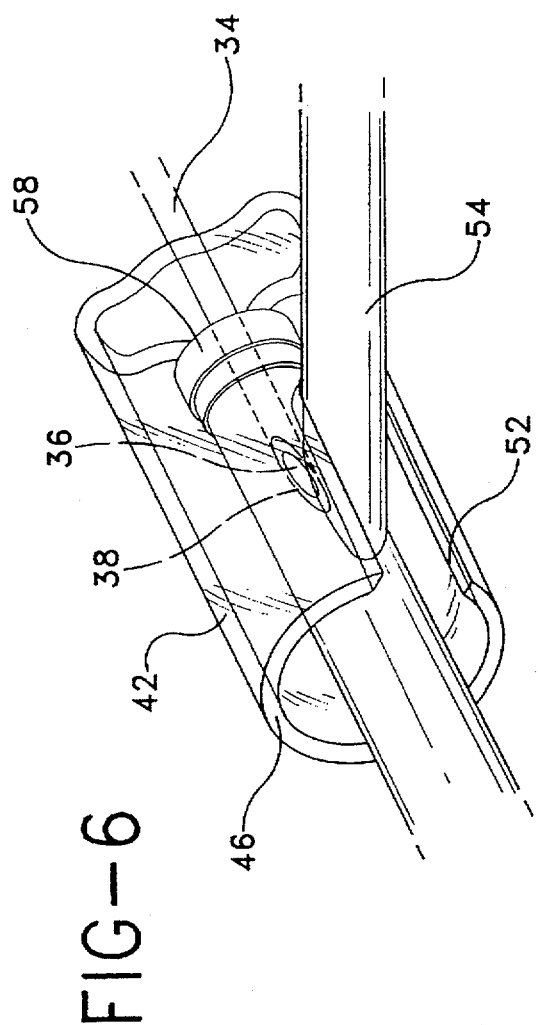

SAFETY SYRINGE WITH I.V. PORT ACCESS

This application is a continuation of application Ser. No. 07/910,196, filed Jul. 8, 1992 now abandoned.

1. Field of Invention

The present invention relates to syringes and more particularly to syringes with a movable shield, which when extended, substantially prevents inadvertent access to the needle.

2. Description of Related Information

Syringes are generally equipped with a sharp pointed needle. The needles are used to penetrate the skin of a patient for administration of a medicament, drawing a specimen or to penetrate a septum for introducing a medicament into a catheter or an I.V. set. In all cases, the sharp point present on a syringe assembly either containing a medicament or having been used on a patient presents some hazard to health care workers and service personnel involved with handling the assembly during and after the usage.

The hazards associated with accidental needle sticks are well known, and will not be described further here. In an effort to reduce or eliminate this problem, many devices have been devised to collect needles after usage, assist reshielding, or provide additional protection to personnel. Many of these devices are significantly more complex than the devices they replace, hence raising the cost and potentially make it more difficult to use the basic syringe and needle device in its intended fashion.

A good system of providing protection for a needle without reshielding is taught in U.S. Pat. No. 4,631,057. The patent teaches a needle guard which initially is in a retracted position around the body or barrel of the syringe allowing the health care workers to use the syringe and needle in a normal fashion for filling and administering the medicament, and then, following the usage, the needle guard is extended from the retracted position to an extended and locked position which obstructs the needle. A syringe manufactured with a guard following the teachings of this patent does not need to be greatly modified, there are only two additional parts required, a collar and the guard itself. Additionally, since the guard constructed using the patent teaching does not involve the needle hub, ordinary needle assembles of many varied sizes and designs can be used with syringes having this type guard.

In addition to the classic use of a syringe with a needle assembly to perform percutaneous punctures for administration of medicaments, many syringes are used to make bolus introductions of medicaments into catheters, I.V. sets, or intermittent infusion sets. In this latter case, the device described in the above referenced patent may have a shortcoming. Once the guard mechanism is extended, access to the needle is substantially prevented. Thus, the guard usually cannot be extended prior to a penetration being made into an infusion device.

In an effort to overcome this problem of shielding a needle intended for use with an injection port, several references can be cited. WO89/10770 teaches a protector shield comprising an arcuate wall, longitudinally positionable about the pointed end of a tubular needle. The arcuate wall has an open side with an arcuate arm which can be used to lock the needle into engagement with a "y-type" injection site. The teachings further suggest that this protector can be assembled with the needle or insert molded as part of the needle hub. Thus a needle with this type of protector, while very useful for connection to injection ports, cannot be used for ordinary percutaneous injections.

U.S. Pat. No. 4,834,716, teaches a protective device for enclosing the scarf of a cannula carried by a boss while permitting access to the scarf by a port of a "y-site" which is located on an adjoining length of flexible tubing as part of an intravenous administration set. Again, while a device constructed according to the this teaching works very well with the other device which is a part of the claimed kit, it cannot be used for percutaneous injections to a patient.

U.S. Pat. No. 4,998,921, teaches a protective sheath for an intermittent I.V. therapy needle. The sheath is a flexible transparent plastic tube having an internal septum which provides two separate interior compartments. One compartment is adapted to house a needle and a portion of the needle hub, providing an enclosed sterile environment when the device is attached to the needle assembly. The second compartment is adapted to be releasably affixed to the exterior of an access port at a "y-site." Again, this device functions effectively for use with an I.V. port, but it is multicomponent, adds complexity to the procedure, is suitable only for use with these type injection ports and cannot be used for percutaneous injections into a patient.

One skilled in the art of syringes, needles, injections and safety can infer from the above presented background material that there remains a need for an invention which is not complex to manufacture, does not interfere with the normal usage of a syringe and needle assembly and is adaptable to usage in a variety of situations, either with direct percutaneous injections to a patient or to injection ports. Further, the device should provide a reliable protection from inadvertent needle sticks without requiring reshielding after use.

SUMMARY OF THE INVENTION

A safety needle device which can be used substantially as a regular syringe or with a "y" type connector. The "y" type connector has a hollow bore within, a sidearm and an injection port with a pierceable septum to provide access to the bore. The device includes an elongate barrel having a longitudinal axis and an inside surface defining a chamber which has an open proximal end, a distal end with a needle cannula having a lumen therethrough in fluid communication with the chamber. The needle cannula projects distally outwardly from the distal end of the barrel and terminates in a distal tip. The device has a needle guard with a proximally located first end and a distally located second end. The needle guard is mounted for movement relative to the barrel from a retracted position in which the guard does not materially obstruct access to the distal tip of the needle cannula and an extended position. In the extended position, the guard substantially prevents inadvertent access to the distal tip of the needle cannula.

The needle guard is releasably retained in the retracted position and locks in the extended position. The needle guard further includes at least one open slot which extends proximally from the second end. The slot is sized to accept the sidearm of a "y" connector when the guard is in the extended position and the needle cannula penetrates the septum of the connector and the bore of the connector is in fluid communication with the chamber of the barrel.

BRIEF DESCRIPTION OF THE DRAWINGS

FIGS. 2, 3 and 4 are cross-sectional views of the safety needle device with the guard in the retracted (2), partially extended (3) and extended (4) positions.

FIGS. 5 and 6 are enlarged details of the distal section of the safety needle device showing the needle guard in the extended (5) position and being used with a "y" connector (6).

DETAILED DESCRIPTION

Figure 1:
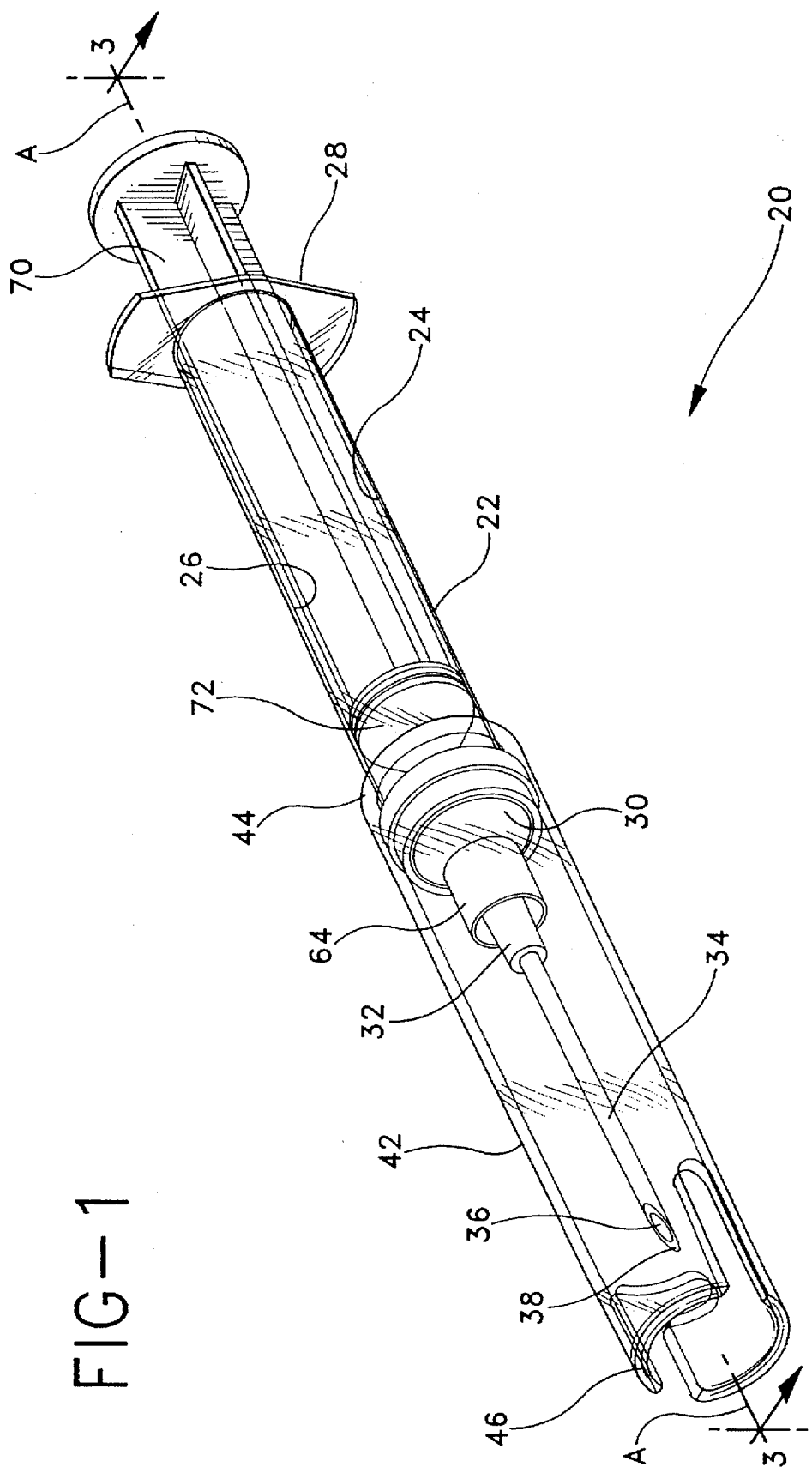
FIG. 1 is a perspective view of a preferred embodiment of the safety needle device with the guard shown in the extended position.

While this invention is satisfied by embodiments in many different forms, there is shown in the drawings and will be described in detail, preferred embodiments of the invention with the understanding that the present disclosure is to be considered exemplary of the principles of the invention and is not intended to limit the invention to the embodiments illustrated. The scope of the invention will be measured by the appended claims and their equivalents.

As is illustrated by FIGS. 1–4, an operable safety needle device 20 of the present invention comprises a barrel 22 having a longitudinal axis A. Barrel 22 is preferably transparent, and has an inside surface 24 defining a chamber 26. Barrel 22 has an open proximal end 28 and a distal end 30. Distal end 30 has a tip 32 having a needle cannula 34 attached. Needle cannula 34 has a lumen 36 in fluid communication with chamber 26. Cannula 34 projects distally outwardly from distal end 30 of barrel 22 and terminates in a distal tip 38, which preferably is a sharpened point, but alternatively may be blunt.

For the purposes of the description of the present invention, the term "distal end" is meant to refer to the end of the device closest to the tip of the needle cannula and the term "proximal end" is meant to refer to the end of the device furthest from that portion of the device where the needle cannula tip is located.

Figure 4:
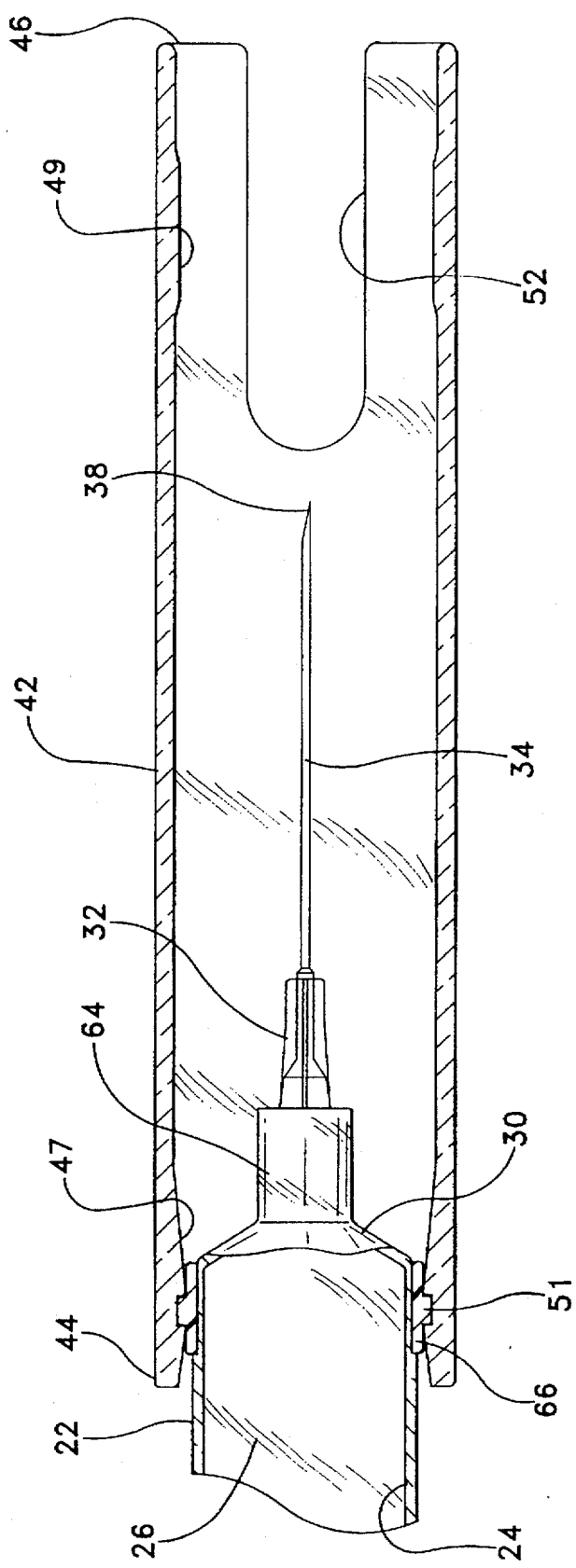

Device 20 includes a needle guard 42 which has a proximally located first end 44 and a distally located second end 46. As is shown in FIG. 2, needle guard 42 is mounted for movement relative to barrel 22 from a retracted position, where guard 42 does not materially obstruct access to needle cannula distal tip 38. As is shown in FIG. 3, guard 42 is in a partially extended position in which guard 42 has moved relative to barrel 22. Then, as is shown in FIG. 4, guard 42 is moved to an extended and locked position in which guard 42 substantially prevents inadvertent access to needle cannula distal tip 38.

Needle guard 42 includes a frictionally engaging mechanism 48 for releasably retaining guard 42 in the retracted position and an interlocking mechanism 50 for locking guard 42 in the extended position. Guard 42 includes open slot 52 extending proximally from second end 46.

As is shown in FIGS. 5 and 6, guard 42 open slot 52 is sized to accept the the sidearm 54 of the "y" connector 56 when guard 42 is in the extended position and needle cannula 34 having distal tip 38 has penetrated the septum 58 of "y" connector 56 and chamber 26 of barrel 22 is in fluid communication with the bore 60 of "y" connector 56. As used in this description and in the appended claims, the term "y" connector is intended to represent intraveneous connectors, heparin locks, infusion apparatus and the like.

Figure 7:
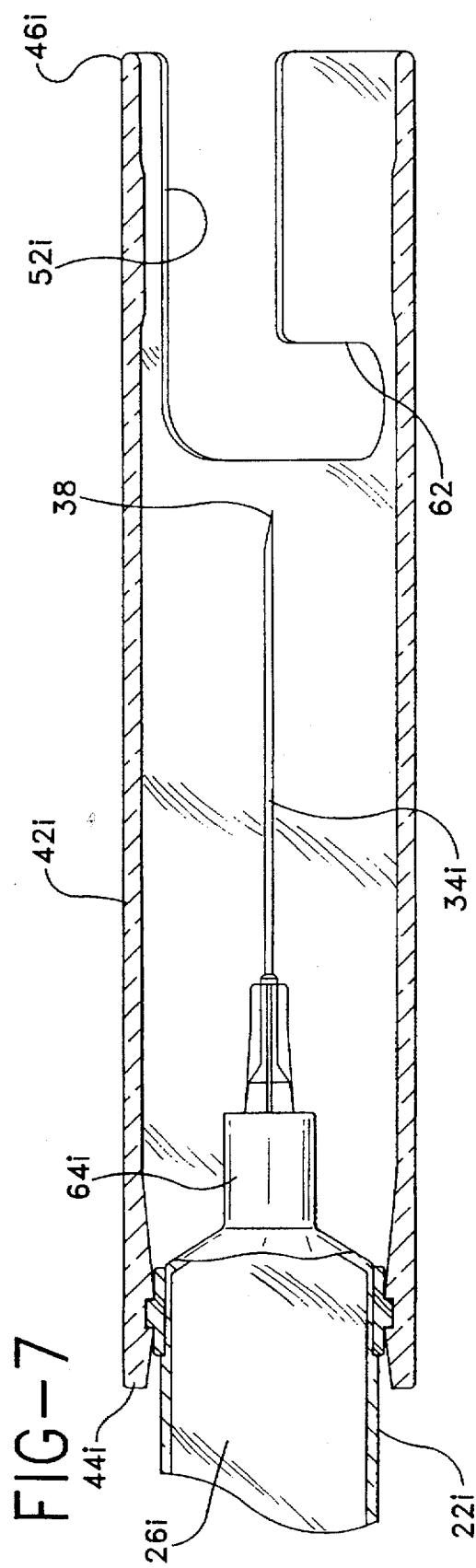
FIGS. 7 and 8 are enlarged details of the distal section of an alternate embodiment of the safety needle device with the needle guard in the extended (7) and being used with a "y" connector (8).
Figure 8:
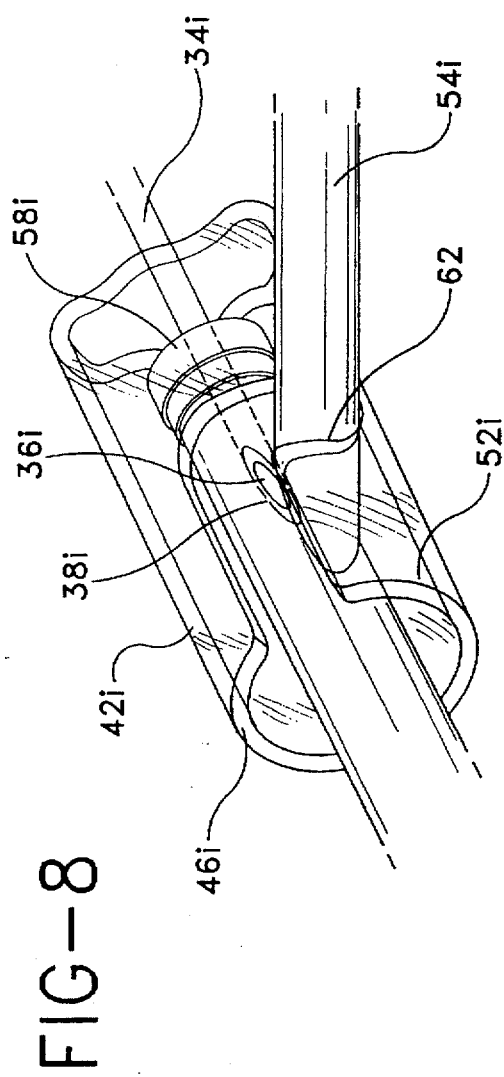

Referring to FIGS. 7 and 8, an alternate embodiment of the safety needle device of the instant invention is shown. In this embodiment the structure of the device is substantially similar to the structure of the embodiment shown in FIGS. 1–6. Accordingly, substantially similar components that perform substantially similar functions will be numbered identically to those components of the embodiments of FIGS. 1–6 except that a suffix "i" will be used to identify those components in FIGS. 7 and 8.

In the alternate embodiment shown in FIGS. 7 and 8, needle guard 42i has a proximally located first end 44i and a distally located second end 46i. Guard 42i has open slot 52i extending proximally from second end 46i. In this alternative embodiment, slot 52i has a "dogleg" portion 62 which is sized to accept sidearm 54i of "y" connector 56i when guard 42i is in the extended position and needle cannula 34i having distal tip 38i has penetrated septum 58i of "y" connector 56i and chamber 26i of barrel 22i is in fluid communication with the bore 60i of "y" connector 56i. The "dogleg" portion is further sized to releasably engage sidearm 54i with a rotational movement of guard 42i—with respect to longitudinal axis A of barrel 22.

Desirably, guard 42 incorporates a plurality of slots 52, and preferably guard 42 includes at least one of a slot 52 which extends proximally from second end 46 and at least one of a slot 52i extending proximally from second end 46i where the slot 52i includes dogleg portion 62. Incorporation of at least one of each of these slot designs allows more varied applications by users without the need for maintaining separate inventories. While the preferred embodiments shown in FIGS. 1–8 suggest a detachable hub 64, the barrel may be supplied with needle cannula 34 fixedly attached to distal tip 32 of barrel 22. In the alternative, barrel 22 may be supplied without a needle but having distal tip 32 designed to accept a standard fitting such as a locking luer type or a slip type luer fitting for subsequent mounting of a needle by the user.

As shown in FIGS. 2, 3 and 4, in the preferred embodiment needle guard 42 is mounted on barrel 22 for movement from the retracted position, through the intermediate position to the extended and locked position relative to barrel 22. It is preferred that the mechanism 48 for releasably retaining guard 42 in the retracted postion includes a collar 66 mounted at distal end 30 of barrel 22 and includes frictionally engaging members. The frictionally engaging members are a first member 47 located on collar 66 and a second member 49 located on guard 42. First member 47 preferably is a flange-like protrusion extending radially outwardly from collar 66. When guard 42 is in the retracted position, member 47 is in frictional engagement with second member 49, which preferably includes a plurality of inwardly projecting axial ribs on the needle guard. The force required to disengage member 47 from member 49 and release guard 42 from the retracted position can be adjusted by varying the amount of interference between members 47 and 49, the materials from which the members are formed and the surface contact area of members 47 and 49.

FIG. 3 shows flange 42 in an intermediate position prior to being fully extended and locked.

In FIG. 4, shows flange 42 in the extended and locked position. It is preferred that mechanism 50 for locking guard 42 in the extended position includes a collar 66 mounted at distal end 30 of barrel 22 and includes interlocking members. The interlocking members are a first member 51 located on collar 66 and a second member 53 located on guard 42. First member 51 preferably is a flange-like protrusion extending radially outwardly from collar 66. When guard 42 is in the extended position, protrusion 51 interlocks with second member 53, which includes a recess to accept and lock first member 51, thereby locking guard 42 in the extended position.

It is further preferred that frictionally engaging member 49 located on guard 42 and interlocking member 53 located on guard 42 both interact with the same single member on collar 66. Flange-like protrusion 47 may be designed both to engage frictionally engaging second member 49 for releasably retaining the guard in the retracted position and to interlock with second interlocking member 53 for locking the guard in the extended position.

Collar 66 may be a discrete part mounted at distal end 30 of barrel 22 or it may be integrally formed as part of barrel 22.

Barrel 22 having proximal open end 28 preferably is supplied with a plunger assembly 70 having a plunger stopper 72, which serves to define fluid tight chamber 26 within barrel 22 by slidably moving along barrel inside surface 24. Plunger assembly 70 serves to draw and expel fluid when moved proximally and distally within the barrel.

Barrel 22 is desirably injection molded from a resin selected from the group consisting of polypropylene, polycarbonate, polyamide, polystyrene, polyvinylchloride and acrylonitrile/butadiene/styrene. Guard 42 is desirably injection molded from a resin selected from the group consisting of polypropylene, polycarbonate, polyamide, polystyrene, polyvinylchloride and acrylonitrile/butadiene/styrene. It is preferred that both barrel 22 and guard 42 be molded from a transparent grade of the material selected to allow visualization of the barrel contents and observation of the needle.

A benefit of the instant safety needle device is that when the guard is in the releasably retained retracted position, the device can be used substantially in any way a standard syringe without a needle guard is used for substantially any procedure or technique. That is, access to the point of the needle cannula is not materially obstructed. When the guard is locked in the extended position, inadvertent access to the needle cannula point is substantially prevented. However, even with the guard in its extended position, it is still possible for the needle cannula distal tip to easily penetrate a septum of most standard "y" or other connectors as desired and further, in some embodiments, releasably engage the sidearm of the connector. Prior art safety needle devices do not offer the ability to function substantially similar to a syringe without the safety capabilities of the instant device while still providing access to the needle cannula distal tip with most standard "y" connectors when the needle guard is in the extended position.

What is claimed is:

1. A safety needle device for use with a "y" type connector, the connector having a hollow bore within, a sidearm and an injection port having a pierceable septum to provide access to the bore, comprising:

an elongate barrel having a longitudinal axis and an inside surface defining a chamber, an open proximal end, a distal end having a needle cannula attached thereto, said needle cannula having a lumen therethrough in fluid communication with said chamber, said needle cannula projected distally outwardly from said distal end of said barrel and terminating in a distal tip;

a needle guard having a proximally located first end and a distally located second end, said needle guard being mounted for movement relative to said barrel from a retracted position in which said guard does not materially obstruct access to said distal tip of said needle cannula and an extended position in which said guard substantially prevents inadvertent access to said distal tip of said needle cannula;

means for releasably retaining said guard in said retracted position;

means for locking said guard in said extended position; and said guard including an open slot extending proximally from said second end, said slot sized to accept the sidearm when said guard is in said extended position, said slot further including a dogleg portion sized to releasably engage the sidearm of the "y" connector with a rotational movement of said guard relative to said axis of said barrel when said needle cannula is penetrating the septum and the bore of the connector is in fluid communication with said chamber of said barrel.

2. The safety needle device of claim 1 wherein said guard has a plurality of slots.

3. The safety needle device of claim 2 wherein at least one of said slots of said guard has a dogleg portion, said dogleg portion sized to releasably engage the sidearm of the "y" connector with a rotational movement of said guard relative to said axis of said barrel when said needle cannula is penetrating the septum and the bore of the connector is in fluid communication with said chamber of said barrel.

4. A safety needle device for use with a "y" type connector, the connector having a hollow bore within, a sidearm and an injection port having a pierceable septum to provide access to the bore, comprising:

an elongate barrel having a longitudinal axis and an inside surface defining a chamber, an open proximal end, a distal end having a needle cannula attached thereto, said needle cannula having a lumen therethrough in fluid communication with said chamber, said needle cannula projecting distally outwardly from said distal end of said barrel and terminating in a distal tip;

a plunger assembly having a stopper slidably positioned in fluid-tight engagement inside said barrel, said plunger capable of moving fluid from said chamber through said lumen upon movement of said plunger toward said distal end, said plunger capable of facilitating the drawing of fluid into said chamber through said lumen upon movement of said plunger away from said distal end;

a needle guard having a proximally located first end and a distally located second end, said needle guard being mounted on said barrel for movement relative to said barrel from a retracted position in which said needle guard does not materially obstruct access to said distal tip of said needle cannula and an extended position in which said guard substantially prevents inadvertent access to said distal tip of said needle cannula;

means for releasably retaining said guard in said retracted position, said means including a collar mounted on said distal end of said barrel and first and second frictionally engaging members located on said collar and said guard respectively, said first member being a flange-like protrusion extending radially outwardly from said collar and said second member including a plurality of inwardly projecting axial ribs on said guard;

means for locking said guard in said extended position, said means for locking including said collar mounted on said distal end of said barrel and interlocking first and second members are located on said collar and said guard respectively, said first member being said flange-like protrusion extending radially outwardly from said collar and said second member including a recess in said guard for receiving said protrusion; and said guard having an open slot extending proximally from said second end, said slot sized to accept the sidearm of the "y" connector when said guard is in said extended position, said slot further including a dogleg portion sized to releasably engage the sidearm of the "y" connector with a rotational movement of the guard relative to said axis of said barrel when said guard is in said extended position and said needle cannula is penetrating the septum of the "y" connector and said chamber of said barrel is in fluid communication with the bore of the connector.

5. A safety needle device for use with a "y" type connector, the connector having a hollow bore within, a sidearm and an injection port having a pierceable septum to provide access to the bore, comprising:

an elongate barrel having a longitudinal axis and an inside surface defining a chamber, an open proximal end, a distal end having a needle cannula attached thereto, said needle cannula having a lumen therethrough in fluid communication with said chamber, said needle cannula projecting distally outwardly from said distal end of said barrel and terminating in a distal tip;

a plunger assembly having a stopper slidably positioned in fluid-tight engagement inside said barrel, said plunger capable of moving fluid from said chamber through said lumen upon movement of said plunger toward said distal end, said plunger capable of facilitating the drawing of fluid into said chamber through said lumen upon movement of said plunger away from said distal end;

a needle guard having a proximally located first end and a distally located second end, said needle guard being mounted on said barrel for movement relative to said barrel from a retracted position in which said needle guard does not materially obstruct access to said distal tip of said needle cannula and an extended position in which said guard substantially prevents inadvertent access to said distal tip of said needle cannula;

means for releasably retaining said guard in said retracted position, said means including a collar mounted on said distal end of said barrel and first and second frictionally engaging members located on said collar and said guard respectively, said first member being a flange-like protrusion extending radially outwardly from said collar and said second member including a plurality of inwardly projecting axial ribs on said guard;

means for locking said guard in said extended position, said means for locking including said collar mounted on said distal end of said barrel and interlocking first and second members are located on said collar and said guard respectively, said first member being said flange-like protrusion extending radially outwardly from said collar and said second member including a recess in said guard for receiving said protrusion; and said guard having a plurality of open slots, said slots extending proximally from said second end of said guard, and sized to accept the sidearm of the "y" connector when said guard is in said extended position and said needle cannula penetrates the septum of the "y" connector and said chamber of said barrel is in fluid communication with the bore of the connector, and at least one of said slots includes a dogleg portion sized to releasably engage the sidearm of the "y" connector with a rotational movement of said guard relative to said axis of said barrel when said guard is in said extended position and said needle cannula is penetrating the septum and the bore of the connector is in fluid communication with said chamber of said barrel.

* * * * *